United States Patent [19]

Sloat

[11] 4,205,955
[45] Jun. 3, 1980

[54] CALCIUM AND MAGNESIUM SPECIFIC HARDNESS METHOD USING ALUMINUM CHELATE EXCHANGE REAGENT

[75] Inventor: Sharon S. Sloat, Urbandale, Iowa

[73] Assignee: HACH Chemical Company, Ames, Iowa

[21] Appl. No.: 946,800

[22] Filed: Sep. 28, 1978

[51] Int. Cl.² .................... G01N 31/22; G01N 33/18
[52] U.S. Cl. ............................................. 23/230 R
[58] Field of Search ............... 23/230 R; 210/38 R, 210/38 A, 38 B

[56] References Cited

U.S. PATENT DOCUMENTS

| | | | |
|---|---|---|---|
| 3,368,969 | 2/1968 | Palen | 23/230 R X |
| 3,496,113 | 2/1970 | Platte et al. | 23/230 R X |
| 3,697,224 | 10/1972 | Means | 23/230 R |
| 3,895,913 | 7/1975 | Bockowski et al. | 23/230 R |

OTHER PUBLICATIONS

Shimizu et al., "Determination of Mg, Fe, Ca, Cu, and Zn by EDTA and Their Application", Chemical Abstracts, No. 17767b, vol. 53, Nov. 1959.

Sherif et al., "Spectrophotometric Determination of Uranium (VI) by the Azide Reaction", Analytica Chimica Acta, 26 (1962), pp. 235–241.

*Primary Examiner*—Arnold Turk
*Attorney, Agent, or Firm*—Leydig, Voit, Osann, Mayer & Holt Ltd.

[57] ABSTRACT

A liquid sample is prepared for measurement of its calcium plus magnesium hardness by adding to the sample an aluminum chelate, preferably aluminum disodium (cyclohexylenedinitrilo) tetra-acetic acid, while maintaining the pH of the sample in the range between about 5 and 8. Interference by iron or copper ions is thereby substantially eliminated without using poisonous substances. The pH of the sample is then raised to between about 9.5 and 11 to insolubilize aluminum ions; a magnesium chelate is added to exchange calcium ions, releasing an equivalent number of magnesium ions; and a dye indicator that forms a colored complex with magnesium ions is added. The calcium plus magnesium hardness is then measured by titration or spectrophotometrically.

24 Claims, 1 Drawing Figure

А4,205,955

CALCIUM AND MAGNESIUM SPECIFIC HARDNESS METHOD USING ALUMINUM CHELATE EXCHANGE REAGENT

BACKGROUND OF THE INVENTION

The present invention relates to methods of measuring the calcium plus magnesium hardness of liquids; and, more particularly, to a method of preparing liquid samples for such measurements.

Titration with (ethylenedinitrilo)tetra-acetic acid (EDTA) is a standard method for measuring calcium plus magnesium hardness of water. (*Standard Methods For The Examination of Water and Wastewater*, pp. 133–37 (11th ed. 1960). In such methods, the calcium plus magnesium hardness is commonly measured in terms of the equivalent concentration of calcium carbonate (mg/l $CaCO_3$).

It is well known that certain metal ions, such as the copper (II) and iron (III) ions interfere in the standard calcium plus magnesium hardness titration procedures. The interference may arise because the metal ions are co-titrated or because they poison the indicator. The mechanism of poisoning is not fully understood. Poisoning may involve formation of metal complexes with the indicator dyes that are relatively stable compared to the chelates the metal ions form with EDTA, resulting in blocking of the indicator and fading or indistinct endpoints. Poisoning may also be caused by an irreversible chemical reaction of the dye which destroys its utility as an indicator. Interference, by whatever mechanism, is a problem in photometric methods as well as in titration methods.

Various reagents have gained acceptance as masking agents or inhibitors for use in reducing the interference of metal ions. For instance, sodium cyanide and potassium cyanide are recognized masking agents, which owe their effectiveness to the fact that cyanide forms very stable complexes with many metal ions. Another recognized reagent is sodium sulfite, which precipitates many metal ions. The usefulness of the cyanide and sulfite reagents is offset, however, because they are highly poisonous. Other masking agents such as cupferron for copper (II) ions and salicylaldoxine for iron (III) ions produce colored species that interfere in photometric methods.

(Cyclohexylenedinitrilo)tetra-acetic acid (CDTA) is used as a masking agent in the method for determining total residual metal ion hardness of boiler water that is described in U.S. Pat. No. 3,895,913. Heavy metal ion interference with the color indicator Calmagite (1-(hydroxy-4-methyl-2-phenylzao)-2 naptho-4-sulfonic acid) is avoided in this method by adding to the sample of boiler water being tested a solution that contains both CDTA and an equimolar portion of a calcium or magnesium salt. CDTA forms stable chelates with magnesium and calcium, and is therefore present as the calcium or magnesium chelate in the solution that is added to the sample. Copper (II), iron (III), and other metal ions that would interfere with the Calmagite dye form chelates with CDTA that are more stable than the magnesium-CDTA or calcium-CDTA chelates. *Stability Constants of Metal-Ion Complexes*, Supplement No. 1, pp. 724–28 (The Chemical Society, 1973). Therefore, in the method described in U.S. Pat. No. 3,895,913, the magnesium or calcium-CDTA chelate functions as an exchange reagent. The CDTA sequesters heavy metal ions and an equivalent number of magnesium or calcium hardness ions are released. This prevents heavy metal interference with the indicator, but since the hardness measurement is based on the number of magnesium and calcium ions present, this method effectively includes these additional heavy metal ions in the hardness value.

SUMMARY OF THE INVENTION

A principal object and aim of the present invention is to provide a method for measurement of the calcium plus magnesium hardness of a liquid sample such that heavy metal ions, such as copper (II) and iron (III), are prevented from interfering with the measurement.

A more particular object is to provide a method of preparing liquid samples for such measurement.

A related object is to provide such a method utilizing an exchange reagent that is compatible with the objective of specifically measuring calcium plus magnesium hardness as opposed to measuring total metal hardness.

A further object is to provide such a method that utilizes a non-poisonous exchange reagent.

Yet another object is to provide such a method that can be used in preparation of a sample for measurement of the magnesium plus calcium hardness by either titration or spectrophotometric methods.

These and other objects will become apparent upon reading the following detailed description, and from the sole FIGURE:

FIG. 1 is a graph of absorbance versus equivalent concentration based on spectrophotometric measurements using water samples of known equivalent concentration.

While the invention will be described in connection with preferred embodiments, it will be understood that the invention is not limited to these specific embodiments. On the contrary, the invention includes all alternatives, modifications, and equivalents as may be included within the spirit and scope of the appended claims.

DETAILED DESCRIPTION

Figure 1:
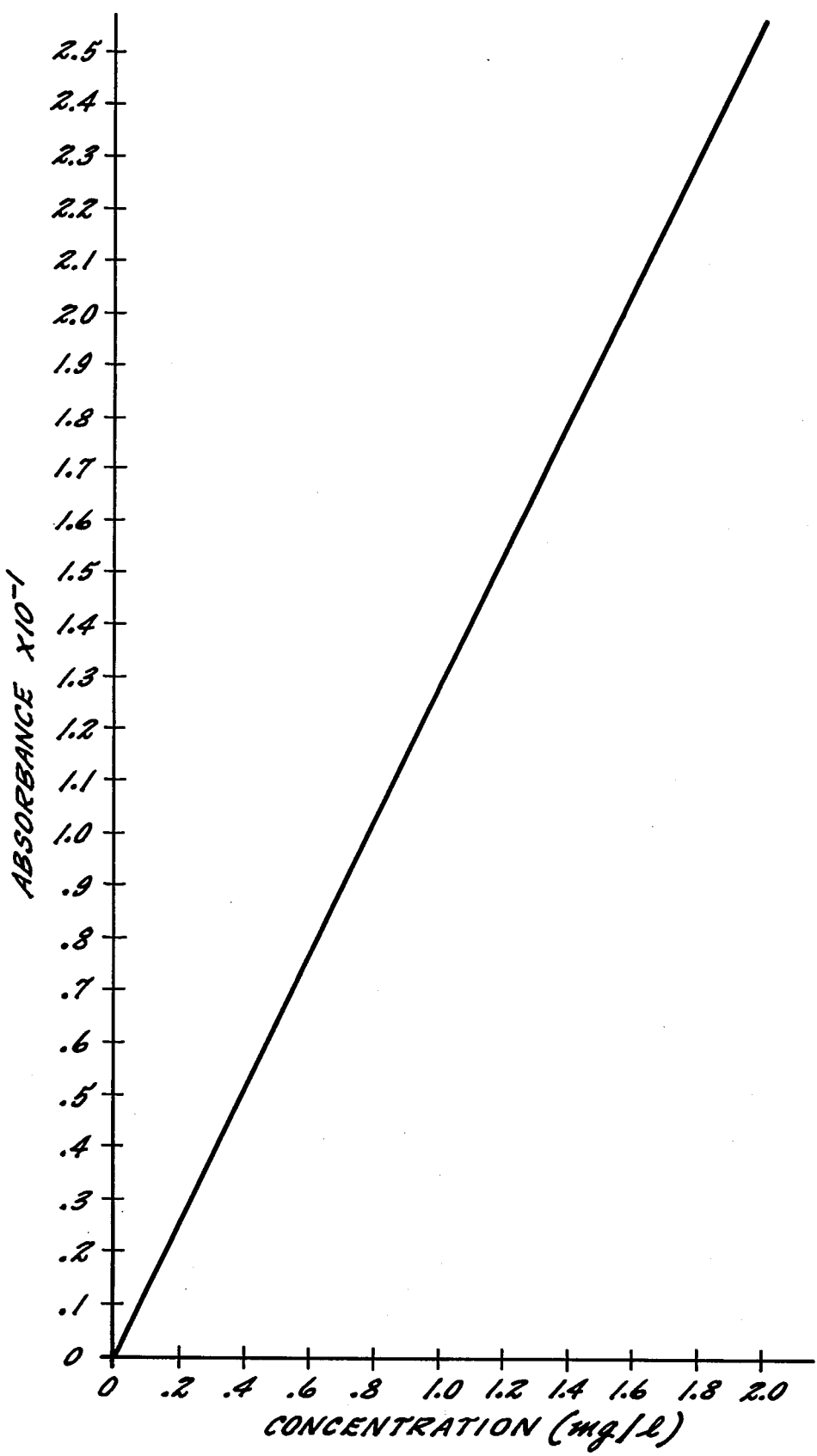

In practicing the present invention, a water sample is prepared for measurement of its calcium plus magnesium hardness as follows. First, free interfering metal ions are eliminated from the sample by use of an exchange reagent. In this step, the pH of the sample is maintained in the range between about 5 and 8, and the exchange reagent is added to the sample.

Pursuant to the present invention, the exchange reagent comprises an aluminum chelate. The principal criteria for selection of the aluminum chelate are that it be non-poisonous, that it be substantially more stable than the analogous calcium and magnesium chelates, and that it be substantially less stable than the analogous iron and copper chelates. Throughout this description, the requirement of a substantial difference in stability means that the values of log K (log of the stability constant) for the chelates or complexes being compared should preferably differ by at least 2. The aluminum chelate is added to the sample in an amount effective to sequester substantially all copper and iron ions present in the sample. Because the aluminum chelate is more stable than the analogous calcium and magnesium chelates, the calcium and magnesium ions present in the sample are not removed.

On a mole basis, the amount of aluminum chelate added to the sample must be at least equivalent to the amount of heavy metal ions (e.g. iron, copper, nickel), present that exchange with the aluminum chelate. Assuming that about 20 ppm of iron ions and 5 ppm of copper ions are present, which is typical for boiler water, it is preferred to add about twice the equivalent amount of aluminum chelate. If a high amount of iron, e.g. 50 ppm, is present, it may be desirable to add less than double the equivalent amount of aluminum chelate. Dissociation of a portion of a large excess of the aluminum chelate may result in removal of a portion of the magnesium ions it is desired to measure. In any case, at least an equivalent amount of the aluminum chelate should be added, and preferably a slight excess amount. If the approximate concentration of heavy metal ions in the sample is not known, the concentration can be determined using standard analytical methods, such as those given in *Standard Methods For The Examination of Water and Wastewater* (11th ed. 1960).

A preferred aluminum chelate is aluminum disodium (cyclohexylenedinitrilo) tetra-acetic acid (Al-CDTA), the preparation of which will be described later. A second example is aluminum disodium (ethylenedinitrilo) tetra-acetic acid (Al-EDTA). Al-EDTA may be advantageously employed if nickel ions are present, because Al-EDTA exchanges nickel more readily than Al-CDTA. However, nickel is normally present in negligible amounts in water samples such as those taken of boiler water, and under such circumstances Al-CDTA is preferred.

The free aluminum ions released by the exchange reagent together with any additional aluminum ions that may be present in the sample must themselves be prevented from interfering with the indicator used. Accordingly, after addition of the exchange reagent, the pH of the sample is raised to between about 9.5 and 11 to substantially completely insolubilize the aluminum ions present in the sample.

Any method for maintaining the pH of the sample within the respective levels required in the foregoing steps that does not interfere with the indicator used or detrimentally affect the relative stabilities of the chelates formed may be used. It is preferred to use a combination of triethanolamine and pyrosulfate to maintain the pH of the sample between about 5 and 8 during addition of the aluminum chelate. After addition of the aluminum chelate, any pH 10 buffer meeting the foregoing criteria may be used to raise the pH of the sample. The preferred pH 10 buffer is an aminomethylpropanol (AMP) buffer composed of approximately 50% aminomethylpropanol with sufficient acetic acid and water added to obtain the desired pH when diluted during its use.

In accordance with a further aspect of the invention, the free calcium ions present in the sample are prevented from reacting with the indicator used by adding to the sample a second exchange reagent that chelates the calcium ions and simultaneously releases an equivalent number of magnesium ions.

Accordingly, a magnesium chelate is next added to the sample. The principal criteria for selection of the magnesium chelate are that it be non-poisonous, and that it be substantially less stable than the analogous calcium, copper, and iron chelates. When these criteria are met, the magnesium chelate exchanges magnesium ions for the calcium ions present in the sample, but does not exchange magnesium ions for iron or copper ions.

The magnesium chelate is added to the sample in an amount that exceeds, on a mole basis, the anticipated amount of calcium ions present in the sample. It is preferred to add about twice the equivalent amount of magnesium chelate. A specific exmple of a suitable magnesium chelate for use in this step is magnesium disodium (cyclohexylenedinitrilo) tetra-acetic acid (Mg-CDTA). A second example is magnesium disodium (ethylenedinitrilo) tetra-acetic acid (Mg-EDTA).

The preparation of the sample is then completed by adding an indicator. The principal criteria for selection of the indicator are that it form a colored complex with magnesium ions that is substantially less stable than the magnesium chelate added in the third step, that any complexes the indicator forms with iron and copper are substantially less stable than the iron and copper chelates produced by addition of the aluminum chelate (i.e.—the first exchange reagent), that any complexes the indicator forms with calcium are substantially less stable than the calcium chelate produced by addition of the magnesium chelate (i.e.—the second exchange reagent) and that in the pH range between about 9.5 and 11 aluminum does not interfere with the indicator. A specific example of a suitable dye indicator is Arsenazo (the trisodium salt of ortho (1, 8-dihydroxy-3, 6 disulfo-2-napthalazo) benzene arsonic acid). Calmagite should not be used, as it reacts with aluminum ions and interfers in spectrophotometric methods of measuring hardness.

Following preparation of a sample in accordance with the foregoing steps, the calcium plus magnesium hardness is determined by measuring the amount of colored magnesium ion-indicator complex present in the samples. This measurement may be effected by titration or spectrophotometric methods. A sample prepared in accordance with the present invention is particularly suited for spectrophotometric methods in that only one relevant color specie is formed, viz.—the magnesium ion-indicator complex.

EXAMPLE 1

This Example illustrates the preparation of Al-CDTA, which is the preferred first exchange reagent.

In a first flask, 393.2 g of aluminum chloride-hexahydrate, were dissolved in one liter of demineralized water, with heat being applied to aid dissolution. 628.6 g of disodium (cyclohexylenedinitrilo) tetra-acetic acid were dissolved in a second flask in one liter of demineralized water. The contents of the two flasks were mixed, and the resulting solution was boiled.

Then, 100 grams of sodium hydroxide were cautiously added to the combined contents of the two flasks, and boiling was continued for 10 minutes.

The solution was evaporated to dryness, and the solid obtained was dried in an oven at 100° C. for 24 hours.

EXAMPLE 2

This Example illustrates a suitable standardization procedure for a spectrophotometric method of determining the calcium plus magnesium hardness of a water sample using Al-CDTA as an exchange reagent.

Standard solutions containing 0, 0.2, 0.4, 0.6, 0.8, 1.0, 1.2, 1.4, 1.6, 1.8, and 2.0 mg/l of $CaCO_3$ were made in 250 ml. plastic volumetric flasks using demineralized water, plastic flasks being used since glass absorbs calcium.

Samples of each of the solutions were then prepared as follows. For each sample, a 50 ml. aliquot of standard solution was added to a plastic 125 ml. flask. To this aliquot, 3 drops of triethanolamine and 0.1 g of pyrosulfate were added to maintain the pH of the sample in the range of from about 5 to 8. The flask was swirled after this addition (and after every subsequent addition) to mix the solution. Then, 0.04±0.01 g of Al-CDTA, as prepared in Example 1, was added. The pH of the sample was raised to between about 9.5 and 11 by addition of a pH 10 AMP buffer. Two drops of 0.1 molar Mg-CDTA solutions were then added to the sample. Finally, 1 ml. of Arsenazo dye (prepared by dissolving 0.75 g of the disodium salt in 1 liter of water) was added to the sample.

The percent transmittance (%T) of each sample was measured at 550 nm, immediately after adding the indicator dye, using a Hach Chemical Co. model DR/2 spectrophotometer (DR/2 instruments are single beam, utilize a circular variable interference filter with a wavelength range of 400 to 700 nanometers, and give photometric reproducibility of ±1%). From the measured values of %T, the absorbance (A) for each sample was calculated using the relation $A = \log_{10}(1)/T$. Values obtained for %T and A for the eleven samples are given in Table 1.

TABLE 1

| CaCo$_3$ mg/l | Transmittance (% T) | Absorbance (A) |
|---|---|---|
| 0 | 99.6 | $1.74 \times 10^{-3}$ |
| 0.2 | 93.8 | $2.78 \times 10^{-2}$ |
| 0.4 | 88.4 | $5.36 \times 10^{-2}$ |
| 0.6 | 83.8 | $7.68 \times 10^{-2}$ |
| 0.8 | 78.9 | $1.03 \times 10^{-1}$ |
| 1.0 | 74.9 | $1.26 \times 10^{-1}$ |
| 1.2 | 70.0 | $1.55 \times 10^{-1}$ |
| 1.4 | 66.1 | $1.80 \times 10^{-1}$ |
| 1.6 | 62.3 | $2.06 \times 10^{-1}$ |
| 1.8 | 58.7 | $2.31 \times 10^{-1}$ |
| 2.0 | 55.4 | $2.57 \times 10^{-1}$ |

FIG. 1 is a plot of absorbance versus concentration of calcium carbonate for the values reported in Table I. As shown, the relationship between absorbance and concentration is linear in this typical concentration range.

EXAMPLE 3

This example illustrates the determination of calcium plus magnesium hardness of a water sample in accordance with the method of the present invention.

When a measurement of calcium plus magnesium hardness is to be made, the Hach DR/2 spectrophotometer is calibrated as follows. Samples of a 0 mg/l and 1.0 mg/l standard CaCO$_3$ solution are prepared in accordance with the procedure in Example 2. The 550 nm wavelength is selected, and the spectrophotometer is adjusted to read 100% T for the 0 mg/l sample. Then, the transmittance of the 1.0 mg/l sample is measured, and, a slight adjustment in the wavelength is made so that this sample measures 75% T.

The samples for which calcium plus magnesium hardness is to be measured are prepared in accordance with the procedure set forth in Example 2. After preparation, a sample is divided into two sample cells. Into one sample cell, there is added one drop of 0.1 M EDTA, which chelates the magnesium ions and thereby eliminates the presence of any colored magnesium ion-indicator complex in this cell. The spectrophotometer is adjusted to read 100% T for this cell. The percent transmittance (%T) for the solution in the remaining sample cell is then measured. This value of %T is converted to absorbence (A), and the magnesium plus calcium hardness is read from the calibration curve, FIG. 1, in terms of the equivalent concentration of CaCO$_3$ (mg/l).

While the invention has been described as applied to measurement of the calcium plus magnesium hardness of water samples, it will be understood that the invention is also applicable to measurement of calcium and magnesium in other solvents that are not reactive with the reagents involved.

Thus, as has been seen, the present invention obviates the problem of interference by heavy metal ions, permits the specific measurement of calcium plus magnesium hardness of liquid samples containing heavy metal ions that would otherwise interfere or be included in the hardness measurement, and eliminates the use of poisonous masking reagents.

What is claimed is:

1. A method of preparing a liquid sample for measurement of its calcium plus magnesium hardness whereby interference by any iron or copper ions that may be present in said sample is substantially eliminated without using poisonous substances, comprising:
   adding to said sample an aluminum chelate that is substantially more stable than the analogous calcium and magnesium chelates and substantially less stable than the analogous iron and copper chelates, in an amount effective for chelation of substantially all copper and iron ions present in said sample.

2. A method in accordance with claim 1 wherein said aluminum chelate is Al-CDTA.

3. A method in accordance with claim 2 wherein the liquid sample is a water sample.

4. A method in accordance with claim 1 wherein said aluminum chelate is Al-EDTA.

5. A method of preparing a liquid sample for measurement of its calcium plus magnesium hardness whereby interference by any iron or copper ions that may be present in said sample is substantially eliminated without using poisonous substances, comprising the steps of:
   (a) while maintaining the pH of said sample in the range between about 5 and 8, adding to said sample an aluminum chelate that is substantially more stable than the analogous calcium and magnesium chelates and substantially less stable than the analogous iron and copper chelates, in an amount effective for chelation of substantially all copper and iron ions present in said samples;
   (b) elevating the pH of the sample and maintaining it at between about 9.5 to 11 to insolubilize the aluminum ions present in said sample.

6. A method in accordance with claim 5 wherein the liquid sample is a water sample.

7. A method in accordance with claim 6 wherein triethanolamine and pyrosulfate are added to said sample in step (a) to maintain the pH of said sample in the range between about 5 and 8 during step (a).

8. A method in accordance with claim 6 wherein a pH 10 buffer comprising about 50% aminomethyl propanol and sufficient acetic acid and water added to obtain the desired pH when diluted during its use is added to the sample in step (b) to maintain the pH of the sample in the range between about 9.5 and 11.

9. A method in accordance with claim 6 wherein said aluminum chelate that is added to said sample in step (a) is selected from the group consisting of Al-CDTA and Al-EDTA.

10. A method of preparing a liquid sample for measurement of its calcium plus magnesium hardness whereby interference by an iron or copper ions that may be present in said sample is substantially eliminated without using poisonous substances, comprising the steps of:

(a) while maintaining the pH of said sample in the range between about 5 and 8, adding to said sample an aluminum chelate that is substantially more stable than the analogous calcium and magnesium chelates and substantially less stable than the analogous iron and copper chelates, in an amount effective for chelation of substantially all copper and iron ions present in said sample;

(b) elevating the pH of the sample and maintaining it at between about 9.5 to 11 to insolubilize the aluminum ions present in said sample;

(c) adding to said sample a magnesium chelate that is substantially less stable than the analogous calcium chelate, and substantially less stable than the copper and iron chelates produced in step (a), in an amount effective for chelation of substantially all calcium ions present in said sample, thereby releasing an equivalent amount of magnesium ions; and, (d) adding to said sample an indicator that forms a colored complex with magnesium ions, said colored complex being substantially less stable than said magnesium chelate added to the sample in step (c), said indicator forming complexes with iron and copper that are substantially less stable than said iron and copper chelates produced in step (a), said indicator forming a complex with calcium that is substantially less stable than said calcium chelate produced in step (c), and said indicator not forming a significant amount of complex with aluminum at the pH established in step (b).

11. A method in accordance with claim 10 wherein the liquid sample is a water sample.

12. A method in accordance with claim 11 wherein said aluminum chelate that is added to said sample in step (a) is Al-CDTA.

13. A method in accordance with claim 11 wherein said aluminum chelate that is added to said sample in step (a) is Al-EDTA.

14. A method in accordance with claim 11 wherein said magnesium chelate that is added to said sample in step (c) is Mg-CDTA.

15. A method in accordance with claim 11 wherein said indicator that is added to said sample in step (d) is Arsenazo.

16. A method in accordance with claim 11 wherein small amounts of triethanolamine and pyrosulfate are added to said sample in step (a) to maintain the pH of said sample in the range between about 5 and 8 during step (a).

17. A method in accordance with claim 11 wherein a pH 10 buffer comprising about 50% aminomethyl propanol and sufficient acetic acid and water added to obtain the desired pH when diluted during use is added to the sample in step (b) to maintain the pH of the sample in the range between about 9.5 and 11.

18. A method of measuring the calcium plus magnesium hardness of a liquid sample whereby interference by any iron or copper ions that may be present in said sample is substantially eliminated without using poisonous substances, comprising the steps of:

(a) while maintaining the pH of said sample in the range between about 5 and 8, adding to said sample an aluminum chelate that is substantially more stable than the analogous calcium and magnesium chelates and substantially less stable than the analogous iron and copper chelates, in an amount effective for chelation of substantially all copper and iron ions present in said sample;

(b) elevating the pH of the sample and maintaining it at between about 9.5 to 11 to insolubilize the aluminum ions present in said sample;

(c) adding to said sample a magnesium chelate that is substantially less stable than the analogous calcium chelate, and substantially less stable than the copper and iron chelates produced in step (a), in an amount effective for chelation of substantially all calcium ions present in said sample, thereby releasing an equivalent amount of magnesium ions;

(d) adding to said sample an indicator that forms a colored complex with magnesium ions, said colored complex being substantially less stable than said magnesium chelate added to the sample in step (c), said indicator forming complexes with iron and copper that are substantially less stable than said iron and copper chelates produced in step (a), said indicator forming a complex with calcium that is substantially less stable than said calcium chelate produced in step (c), and said indicator not forming a significant amount of complex with aluminum at the pH established in step (b); and (e) measuring the amount of said colored complex present in said sample.

19. A method in accordance with claim 18 wherein step (e) is performed spectrophotometrically.

20. A method in accordance with claim 18 wherein step (e) is performed by titration.

21. A method in accordance with claim 18 wherein the liquid sample is a water sample.

22. A method in accordance with claim 21 wherein said aluminum chelate that is added in step (a) is Al-CDTA.

23. A method in accordance with claim 21 wherein said aluminum chelate that is added in step (a) is Al-EDTA.

24. A method in accordance with claim 21 wherein said magnesium chelate that is added in step (c) is Mg-CDTA.

* * * * *